(12) United States Patent
Kumar

(10) Patent No.: US 11,660,423 B2
(45) Date of Patent: May 30, 2023

(54) CATHETER SYSTEM WITH EXTENDABLE EXTENSION TUBE

(71) Applicant: Becton, Dickinson and Company, Franklin Lakes, NJ (US)

(72) Inventor: Jithendra Kumar, Woodlands (SG)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 16/989,293

(22) Filed: Aug. 10, 2020

(65) Prior Publication Data

US 2021/0060306 A1    Mar. 4, 2021

Related U.S. Application Data

(60) Provisional application No. 62/892,725, filed on Aug. 28, 2019.

(51) Int. Cl.
| | |
|---|---|
| *A61M 25/06* | (2006.01) |
| *A61M 25/00* | (2006.01) |
| A61M 25/02 | (2006.01) |

(52) U.S. Cl.
CPC .... *A61M 25/0606* (2013.01); *A61M 25/0023* (2013.01); *A61M 25/0625* (2013.01); *A61M 25/0662* (2013.01); *A61M 25/0693* (2013.01); *A61M 2025/0253* (2013.01); *A61M 2025/0681* (2013.01)

(58) Field of Classification Search
CPC .......... A61M 25/0606; A61M 25/0023; A61M 25/0625; A61M 25/0662; A61M 25/0693; A61M 25/0631; A61M 25/0637; A61M 2025/0253; A61M 2025/0681
See application file for complete search history.

(56) References Cited

U.S. PATENT DOCUMENTS

| 4,362,156 A | | 12/1982 | Feller et al. | |
|---|---|---|---|---|
| 4,795,432 A | * | 1/1989 | Karczmer | ........... A61M 5/3257 604/110 |
| 2007/0088323 A1 | * | 4/2007 | Campbell | ............. A61M 25/10 604/523 |

(Continued)

FOREIGN PATENT DOCUMENTS

| EP | 2484402 | 8/2012 |
|---|---|---|
| EP | 2905042 | 8/2015 |

(Continued)

*Primary Examiner* — Kami A Bosworth
*Assistant Examiner* — Antarius S Daniel
(74) *Attorney, Agent, or Firm* — Kirton Mcconkie; Whitney Blair; Kevin Stinger

(57) ABSTRACT

A catheter system may include a catheter adapter having a distal end, a proximal end, and a lumen extending therebetween. The system may include a catheter tube extending distally from the catheter adapter. The system may include an extension tube coupled to the proximal end of the catheter adapter. The extension tube may be extendable. The system may include a locking mechanism coupled to the extension tube and removably coupled to the proximal end of the catheter adapter. The system may include a needle hub removably coupled to a proximal end of the extension tube and an introducer needle extending through the catheter tube. A proximal end of the introducer needle may be secured within the needle hub.

16 Claims, 11 Drawing Sheets

(56) References Cited

U.S. PATENT DOCUMENTS

| | | | |
|---|---|---|---|
| 2012/0016307 A1* | 1/2012 | Burkholz | A61B 5/150519 |
| | | | 604/168.01 |
| 2012/0053523 A1* | 3/2012 | Harding | A61M 25/0612 |
| | | | 604/164.08 |
| 2013/0158506 A1* | 6/2013 | Harris | A61M 25/0693 |
| | | | 604/506 |
| 2017/0120011 A1* | 5/2017 | Burkholz | A61M 25/0606 |
| 2017/0120014 A1* | 5/2017 | Harding | A61M 25/065 |

FOREIGN PATENT DOCUMENTS

| | | | | |
|---|---|---|---|---|
| WO | WO-2011044296 A1 * | 4/2011 | | A61M 25/0021 |
| WO | 2017/074680 | 5/2017 | | |
| WO | 2017/074682 | 5/2017 | | |

\* cited by examiner

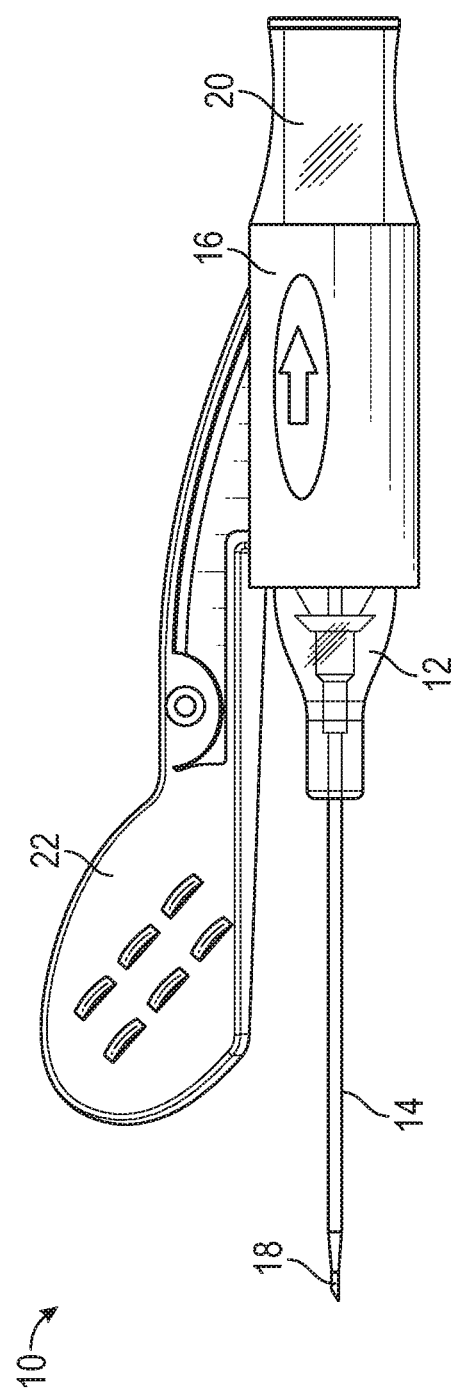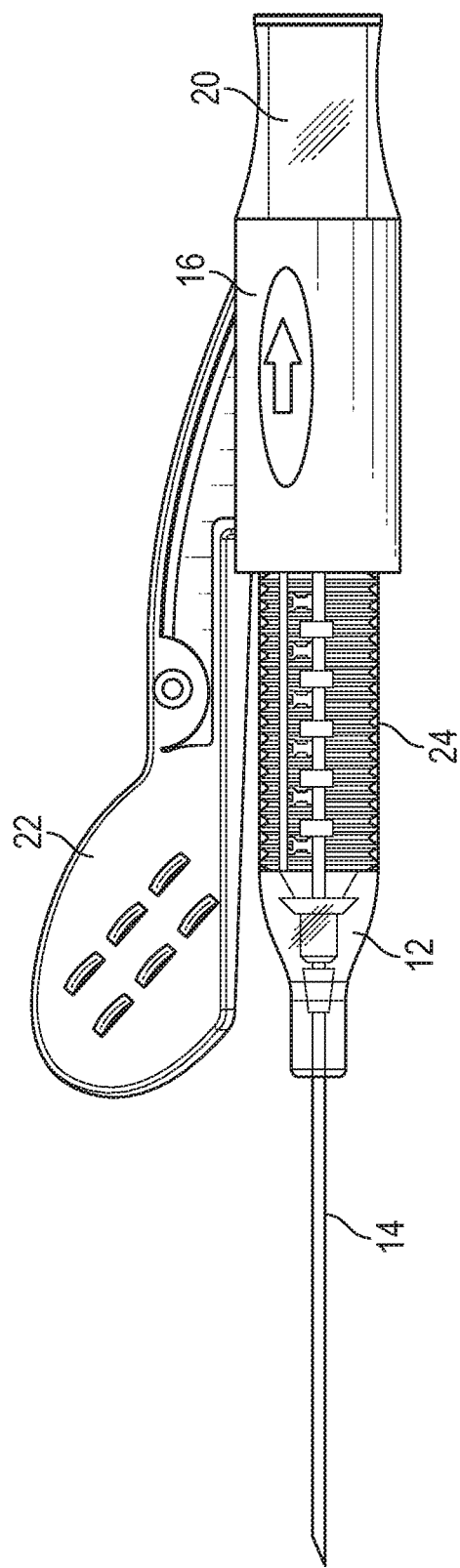
FIG. 1A
FIG. 1B

CATHETER SYSTEM WITH EXTENDABLE EXTENSION TUBE

RELATED APPLICATIONS

This application claims the benefit of U.S. Patent Application No. 62/892,725, filed Aug. 28, 2020 and entitled CATHETER SYSTEM WITH EXTENDABLE EXTENSION TUBE which is incorporated herein in its entirety.

BACKGROUND

Infusion therapy, a common healthcare procedure, may be facilitated by a vascular access device. For example, hospitalized, home care, and other patients receive fluids, pharmaceuticals, and blood products via a vascular access device inserted into the vascular system. Blood withdrawal is another common healthcare procedure that may be facilitated by a vascular access device.

A vascular access device may access a peripheral or central vasculature of a patient. A vascular access device may be indwelling for short term (days), moderate term (weeks), or long term (months to years). A vascular access device may be used for continuous infusion therapy or for intermittent therapy.

A common type vascular access device is an over-the-needle peripheral intravenous catheter (PIVC). As its name implies, the "over-the-needle" PIVC may be mounted over an introducer needle having a sharp distal tip. The sharp distal tip may be used to pierce skin and the vasculature of the patient. Insertion of the PIVC into the vasculature may follow the piercing of the vasculature by the needle. The needle and the PIVC are generally inserted at a shallow angle through the skin into the vasculature of the patient with a bevel of the needle facing away from the skin of the patient.

Placement of the PIVC within the vasculature is essential for blood withdrawal and fluid infusion and yet may be difficult to maintain. Patients often want or need to have a normal range of body motion while the PIVC is inserted. Also, external objects may apply external forces to the PIVC and thereby shift the PIVC's location within the vasculature. In some instances, the external forces may cause back-and-forth dynamic movement of a tip of the PIVC or a static shift in the tip from its location within the vasculature.

The PIVC assembly may be coupled with an extension set, which may allow coupling of an infusion or blood withdrawal device at a location removed from an insertion site of the PIVC. While the extension set may reduce a risk of disturbing the insertion site or dislodging the catheter from the vasculature of the patient, an extension set requires a priming protocol, wherein the extension tube must be filled with fluid to eliminate the air bubbles in a catheter system. The priming procedure is time consuming for a clinician. Further, a catheter having a lengthy extension tube has potential to get caught and accidentally dislodge the catheter or requires more securement that may feel bulky and uncomfortable to a patient. Lastly, a catheter with an extension tube requires a longer length to loop the tube for proper securement to minimize kinking. Therefore, a catheter system with an extendable extension tube would be beneficial to clinicians and patients requiring infusion therapy.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates to catheter systems configured to facilitate catheter insertion success and eliminate or significantly reduce priming and also improve patient comfort related to catheter securement for longer indwell times. In further detail, the catheter system may reduce complications that may be associated with insertion of a catheter tube into a vein of a patient and/or improve the indwelling time of the catheter and looping of extension tubing. The catheter system may also eliminate or significantly reduce time associated with priming in order for clinicians to expedite PIVC setup.

In some embodiments, a catheter system may include a catheter adapter having a distal end, a proximal end, and a lumen extending therebetween. The catheter system may include a catheter tube extending distally from the catheter adapter. The catheter system may include an extension tube coupled to the proximal end of the catheter adapter. In some embodiments, the extension tube may be extendable. In some embodiments, the catheter system may include a locking mechanism coupled to the extension tube and removably coupled to the proximal end of the catheter adapter. The system may include a needle hub removably coupled to a proximal end of the extension tube and an introducer needle extending through the catheter tube. In some embodiments, a proximal end of the introducer needle may be secured within the needle hub.

In some embodiments, the extension tube may be corrugated. The extension tube may be flexible when extended, such that the extension tube may bend in various directions as required by the infusion therapy. Further, the extension tube may be resilient and retains shape when curved and may resist kinking.

In some embodiments, the locking mechanism includes a lever having a lip disposed on a distal end of the locking mechanism that engages with a flange disposed on the catheter adapter. For example, in response to a depression of a proximal end of the lever, the lip may disengage from the flange of the catheter adapter. In some embodiments, the extension tube may be compressed when the locking mechanism is engaged and is extendable when the locking mechanism is disengaged. The introducer needle may be withdrawable through the extension tube when the extension tube is either compressed, extended, or while the extension tube is being extended.

In some embodiments, the catheter system may include a septum. The septum may be disposed within a proximal end of the extension tube. In other embodiments, the catheter system may include a luer connector coupled to the proximal end of the extension tube. A flash chamber may be disposed within the proximal end of the needle hub. In response to insertion of the catheter tube into the vein of the patient, blood may flow into the flash chamber. The flash chamber may include an air vent. In some embodiments, the flash chamber may extend in a proximal direction from the proximal end of the needle hub. The flash chamber may have a capacity between about 2 ml to about 3 ml. In some embodiments, the flash chamber may be transparent.

In some embodiments, the needle hub may include a paddle grip. Further, the catheter adapter may include at least one wing that extends outwardly from the catheter adapter. The at least one wing may include an upper surface and a lower surface. In some embodiments, the upper surface of the wing includes a grip and the lower surface of the wing includes a recess. The recess may couple with a grip on an upper surface of the paddle grip when a tip of the introducer needle is withdrawn within the catheter tube.

It is to be understood that both the foregoing general description and the following detailed description are exemplary and explanatory and are not restrictive of the embodiments of the present disclosure, as claimed. It should be understood that the various embodiments of the present disclosure are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which:

FIG. 1A is a perspective top view of an example catheter system 10, according to some embodiments;

FIG. 1B is a perspective top view of an example catheter system 10, illustrating an extended extension tube, according to some embodiments;

Figure 2A:
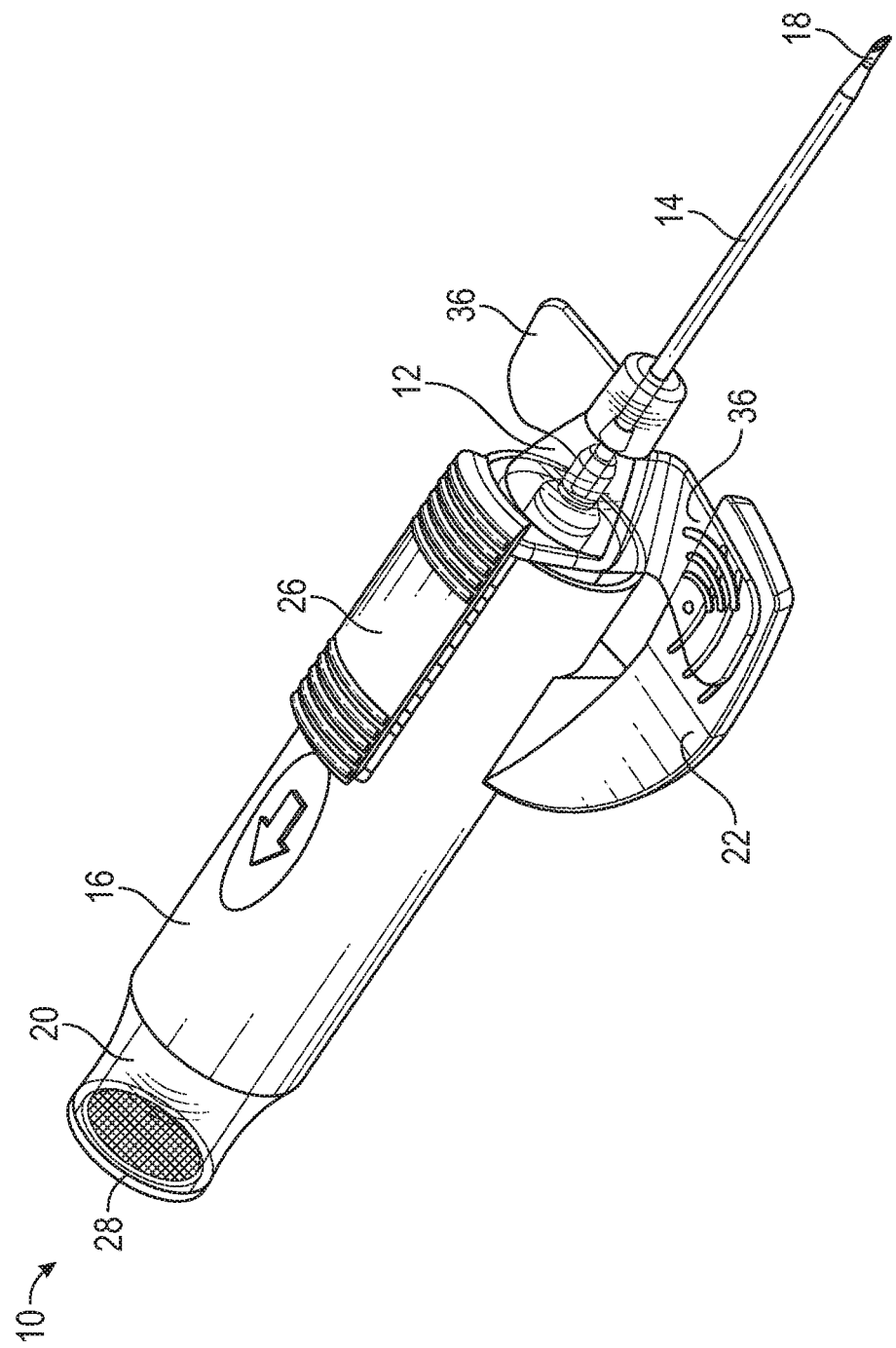
FIG. 2A is a front perspective view of an example catheter system, according to some embodiments.

It is to be understood that the Figures are for purposes of illustrating the concepts of the present disclosure and may not be drawn to scale. Furthermore, the Figures illustrate exemplary embodiments and do not represent limitations to the scope of the present disclosure.

DESCRIPTION OF EMBODIMENTS

Exemplary embodiments of the present disclosure will be best understood by reference to the Figures, wherein like parts are designated by like numerals throughout. It will be readily understood that the components of the present disclosure, as generally described and illustrated in the Figures herein, could be arranged and designed in a wide variety of different configurations. Thus, the following more detailed description of the embodiments of the apparatus and systems, as represented in the Figures, is not intended to limit the scope of the present disclosure, as claimed in this or any other application claiming priority to this application, but is merely representative of exemplary embodiments of the present disclosure.

The present disclosure relates generally to a catheter system configured to facilitate catheter insertion success, eliminate or significantly reduce priming, and improve patient comfort related to catheter securement for longer indwell times. Referring now to FIG. 1A, an example catheter system 10 is illustrated, ready for insertion into a vein of a patient (not shown in FIG. 1A). In some embodiments, the catheter system 10 may include a catheter adapter 12 and a catheter tube 14. The catheter adapter 12 may include a distal end, a proximal end, and a lumen extending therebetween. The catheter tube 14 may extend distally from the catheter adapter 12.

The catheter system 10 may include a needle hub 16. The proximal end of the catheter adapter may be removably coupled to the needle hub 16. The catheter system 10 may include an introducer needle 18. In some embodiments, the introducer needle 18 may extend through the catheter tube 14 and a proximal end of the introducer needle 18 may be secured within the needle hub 16.

A flash chamber 20 may be disposed within and extend in a proximal direction from the proximal end of the needle hub 16. In some embodiments, the flash chamber 20 may be transparent such that a clinician is able to verify that the catheter has been properly inserted into the vein of the patient. In some embodiments, the needle hub 16 further includes a paddle grip 22 to aid in the handling of the needle hub. The paddle grip 22 may extend outwardly from the needle hub 16 and in a distal direction.

Referring now to FIG. 1B, the catheter system 10 may include an extension tube 24 coupled to the proximal end of the catheter adapter 12. The extension tube 24 may be extendable and may be corrugated. The extendable and/or corrugated extension tube 24 may reduce or eliminate the need for priming of the catheter system 10 by reducing the internal fluid volume, such that external fluids are not required to prevent air bubbles forming in the catheter system 10.

Figure 2B:
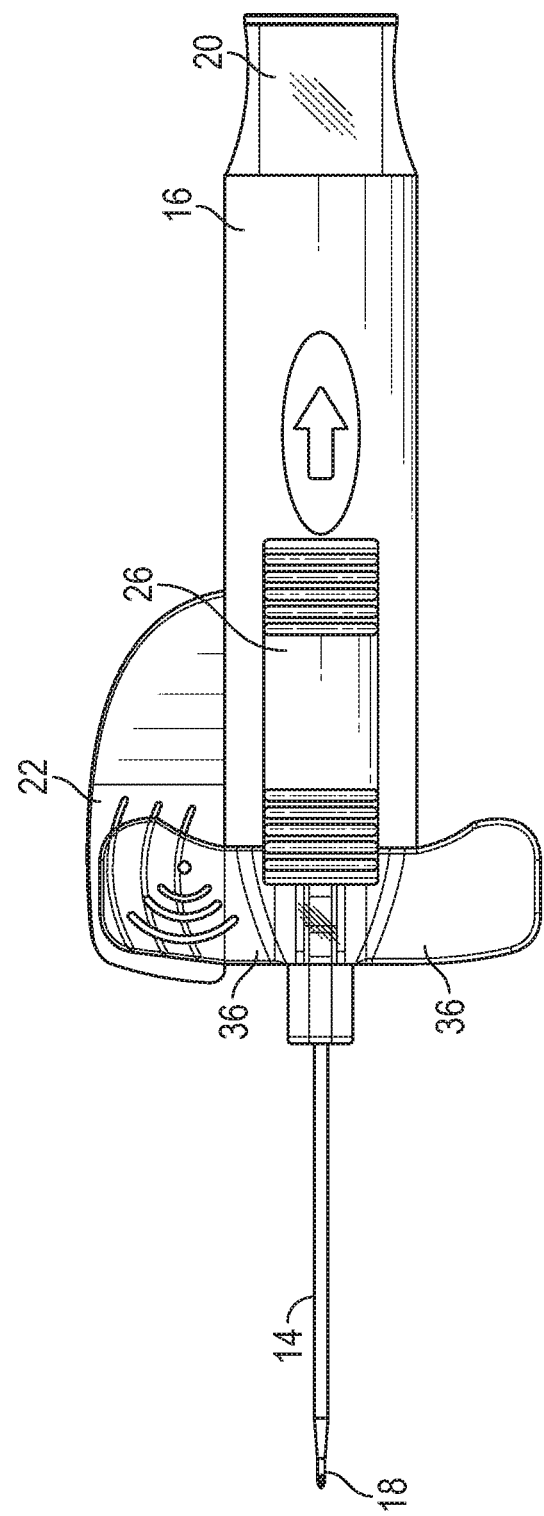
FIG. 2B is a top plan view of the catheter system of FIG. 2A.
Figure 2C:
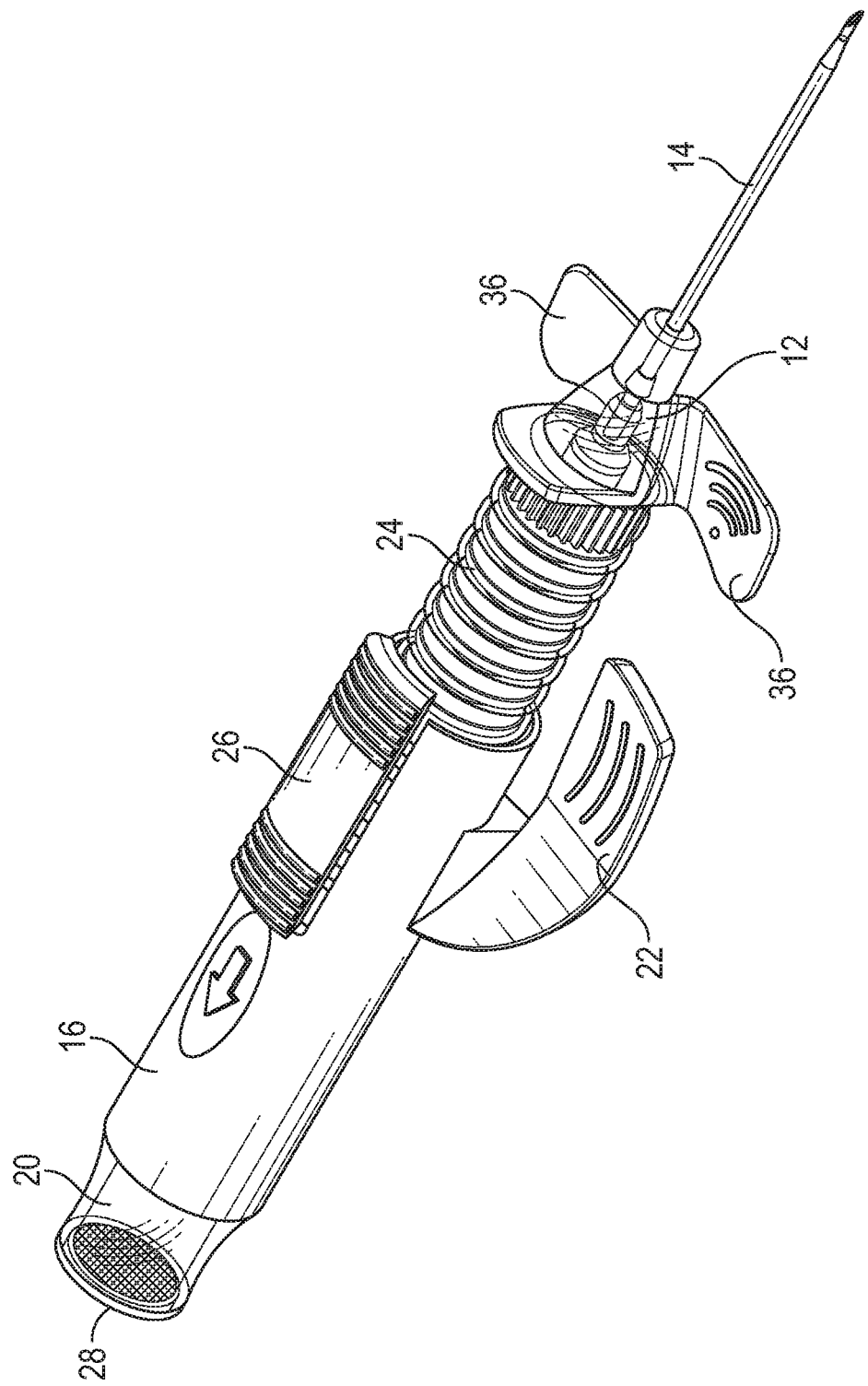
FIG. 2C is a perspective view of the catheter system of FIG. 2A with an extended extension tube.

Referring now to FIGS. 2A-2C, in some embodiments, the catheter system 10 may include a locking mechanism 26 coupled to the extension tube and removably coupled to the proximal end of the catheter adapter 12. The locking mechanism 26 may be located on an upper surface of the catheter system 10. The locking mechanism may include ridges to grip and also provide indication of proper locations to apply pressure to operate the locking mechanism 26. The locking mechanism 26 may be engaged to maintain the extension tube 24 in a compressed state and disengaged for the extension tube 24 to be extended. For example, the extension tube 24 may include a lever. The lever may be depressed on one end to disengage the locking mechanism 26.

In some embodiments, the locking mechanism 26 may include a lip disposed on a distal end of the lever to function as the locking mechanism 26. The catheter adapter 12 may include a flange extending upward. The flange may include a flat, rigid plastic extending from the catheter adapter 12 so that the locking mechanism may engage with the flange disposed on the catheter adapter 12. In some embodiments, a user may apply pressure to a proximal end of the locking mechanism lever to raise the lip and disengage the lip from the flange.

In some embodiments, at least a portion of the proximal end of the catheter adapter 12, the flash chamber 20, and the extension tube 24 may nest within at least a portion within the needle hub 16. The catheter adapter 12 and the extension tube 24 may be housed within the needle hub 16 prior to using the catheter adapter 12 on a patient and/or expanding the extension tube 24. The compact design of the catheter system 10 may enable a user to insert the catheter tube 14 into a vein using a single hand.

In some embodiments, a proximal end of the catheter adapter 12 is slidably coupled to a distal end of the needle hub 16. The extension tube 24 may be housed completely within the needle hub 16 while the extension tube 24 is compressed. In some embodiments, the locking mechanism may be configured to be a push-pull slider to extend and compress the extension tube 24 and/or separate the catheter adapter 12 and the extension tube 24 from the needle hub 16. For example, a user may remove the catheter adapter 12 from the needle hub 16 by applying a force distally to the locking mechanism 26 to slide the extension tube 24 and the catheter adapter 12 from the needle hub 16.

The locking mechanism 26 may be coupled to a proximal end of the extension tube 24. Thus, when the needle hub is separated from the extension tube 24, the locking mechanism 26 remains coupled to the distal end of the extension tube. The needle hub may include a portion on an upper surface of the needle hub that is cutout, such that the locking mechanism 26 may slide distally to be removed and for the locking mechanism 26 to be accessible to a user.

In some embodiments, the flash chamber 20 may include an air vent 28. The air vent 28 may be permeable to gases and impermeable to fluids. The air vent may be configured to remove gases from the flash chamber 20 as blood or other fluid enters the chamber. In some embodiments, the flash chamber 20 may be disposed within a proximal end of the needle hub. In response to insertion of the catheter tube 14 into the vein of the patient, blood may flow into the flash chamber 20 and provides an indication of successful placement of introducer needle 18 and/or the catheter tube 14 within the vein. In some embodiments, at least a portion of the flash chamber extends from the proximal end of the needle hub 16 and may be transparent. The flash chamber 20 may be transparent to provide a flashback indication of successful insertion into the vein of the patient.

Figure 2D:
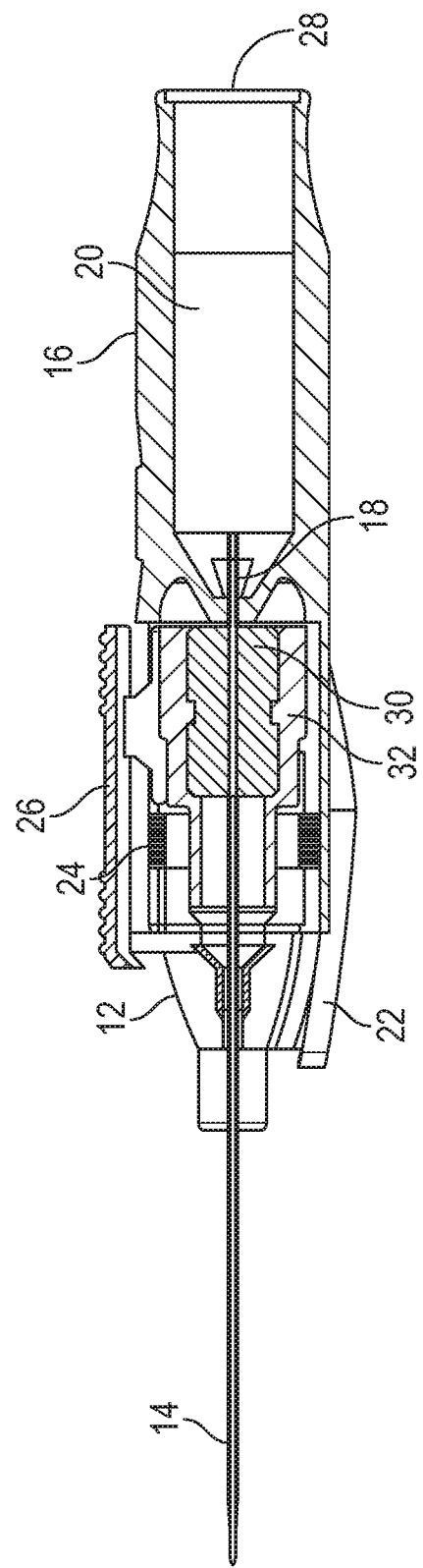
FIG. 2D is a cross-sectional side view of the catheter system of FIG. 2A.
Figure 2E:
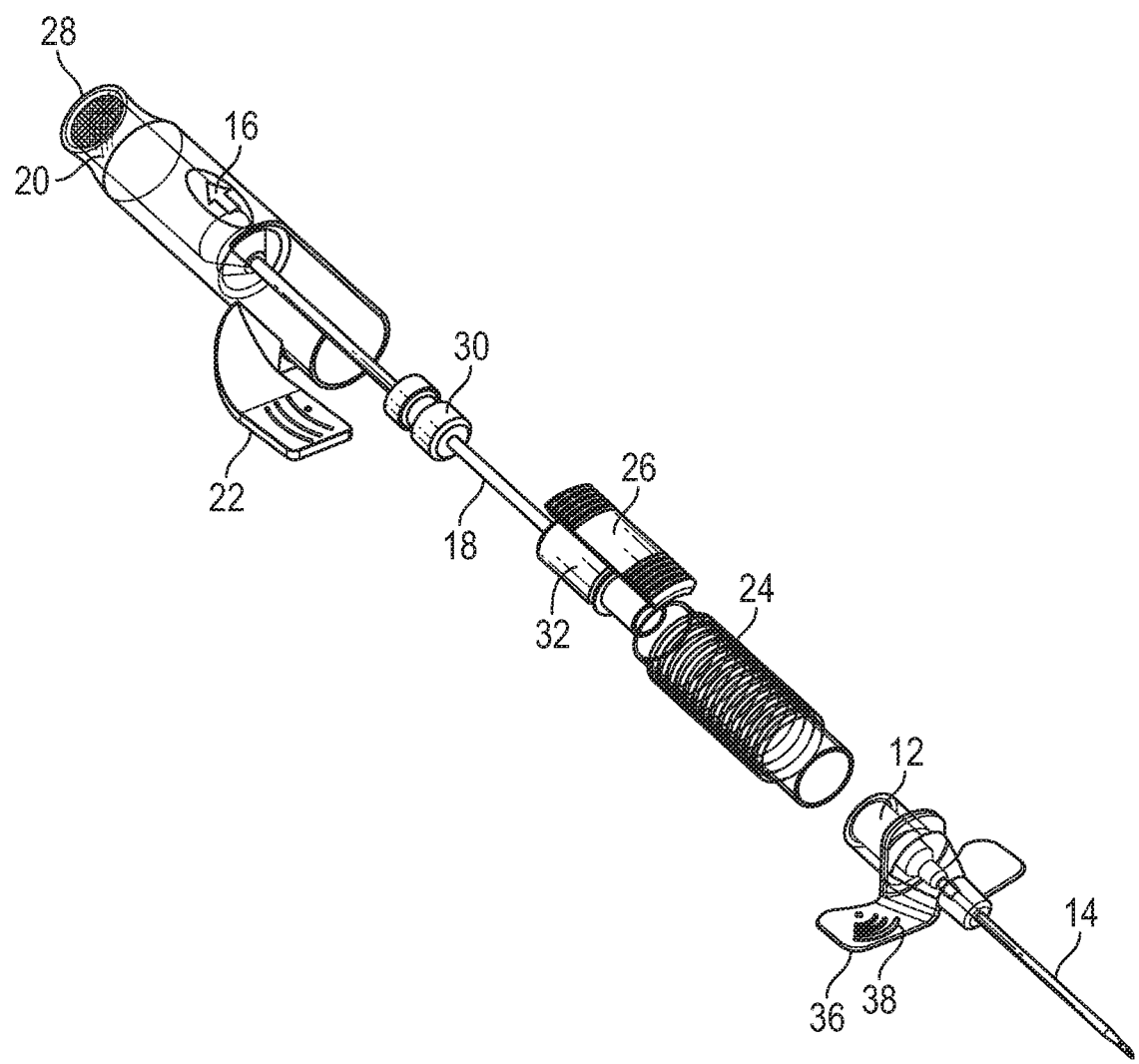
FIG. 2E is an exploded view of the catheter system of FIG. 2A.
Figure 3A:
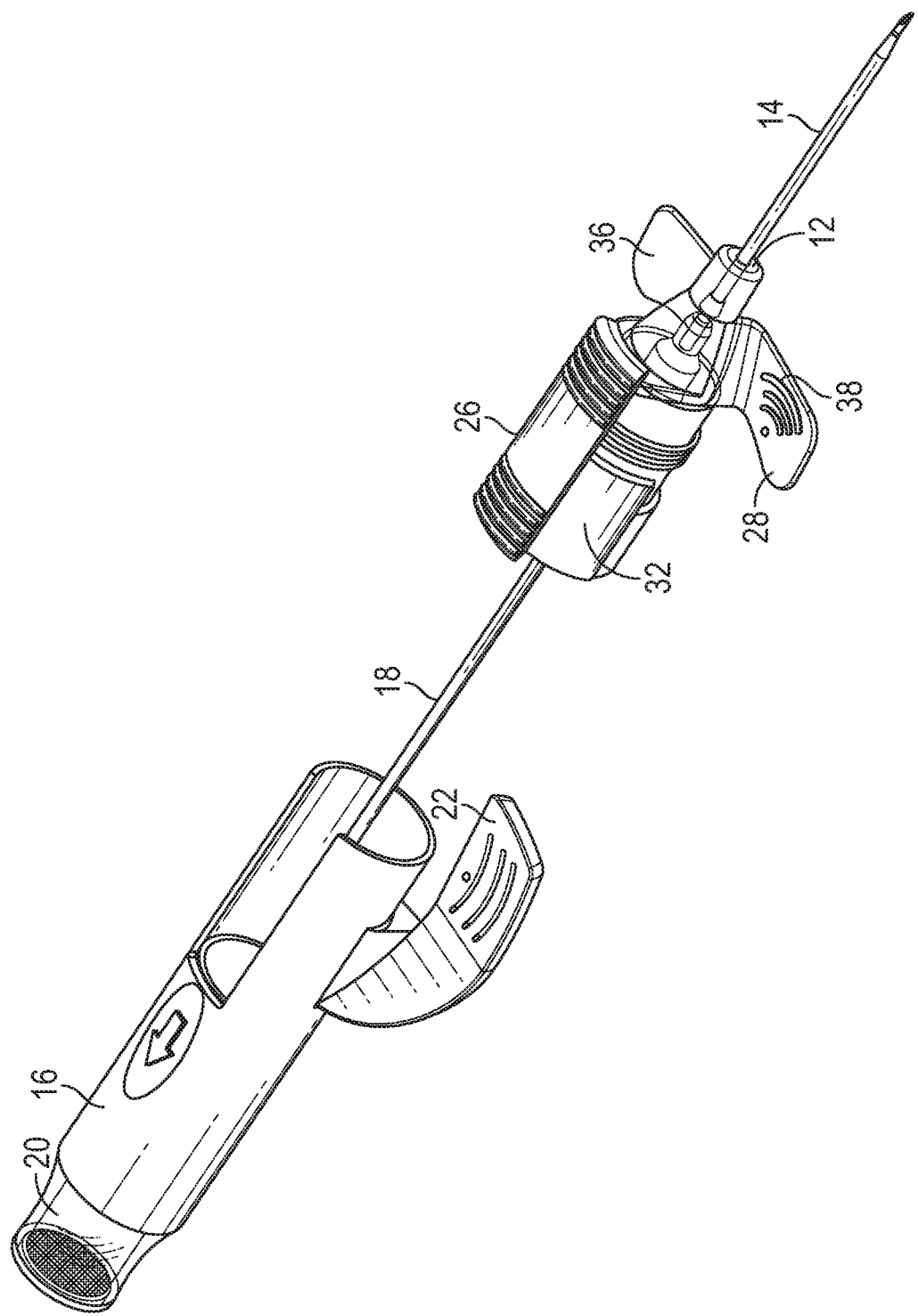
FIG. 3A is a perspective view of an the catheter system of FIG. 2A with the needle hub partially separated from the catheter adapter.
Figure 3B:
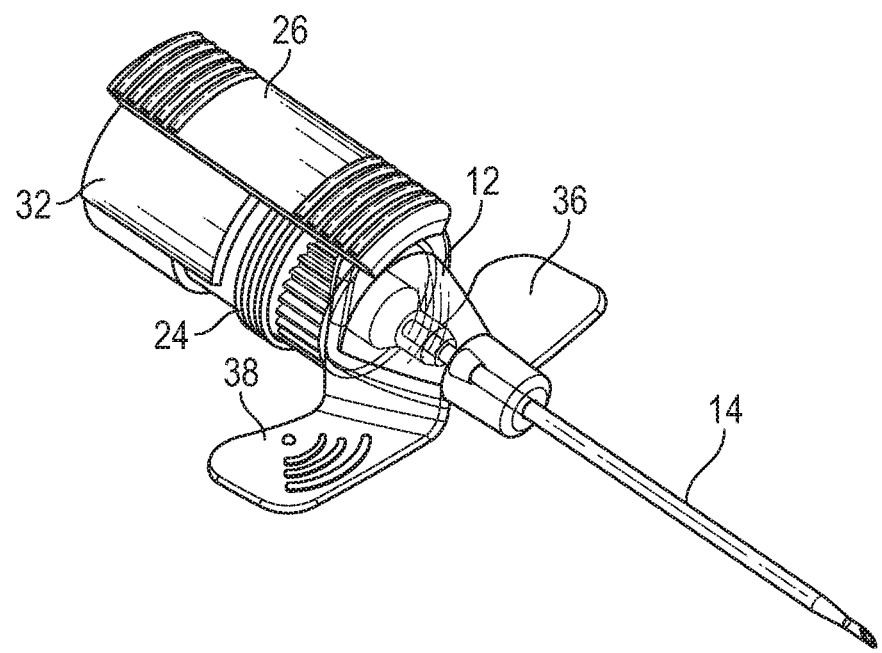
FIG. 3B is a perspective view of an example catheter adapter and extension tube with the extension tube compressed, according to some embodiments.
Figure 3C:
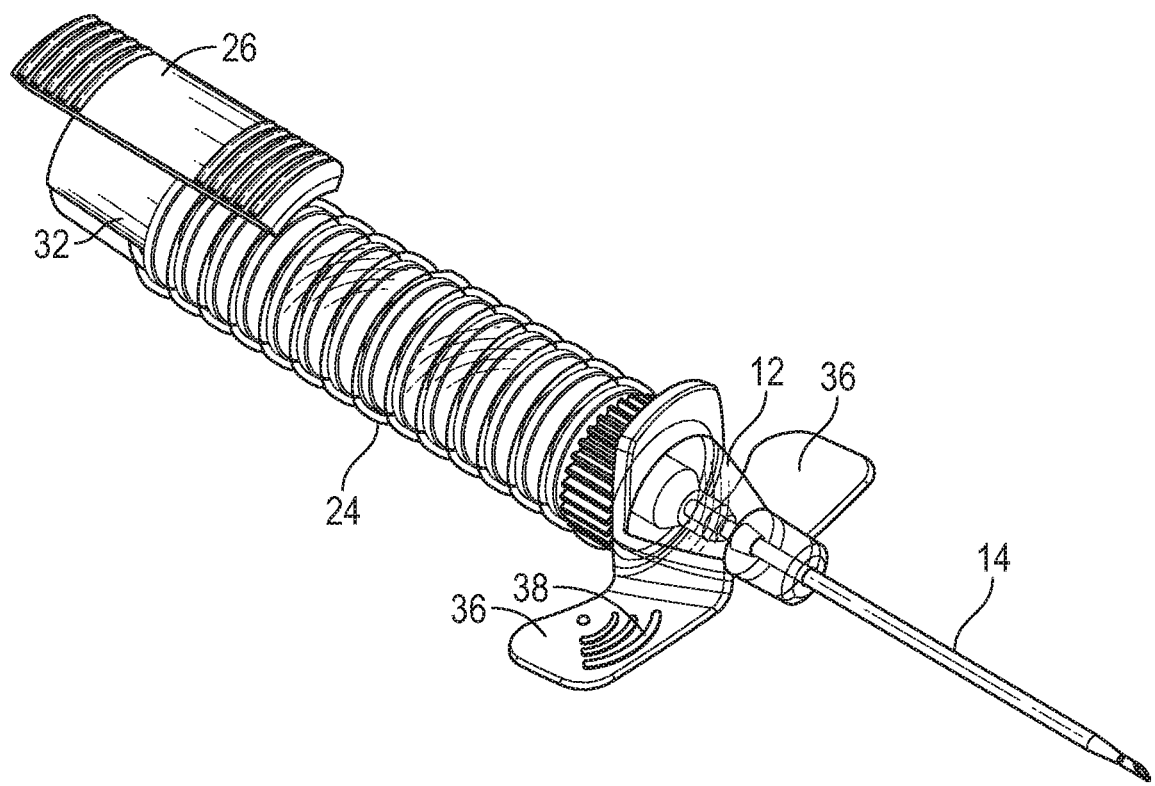
FIG. 3C is a perspective view of the catheter adapter of FIG. 3B with the extension tube extended.
Figure 3D:
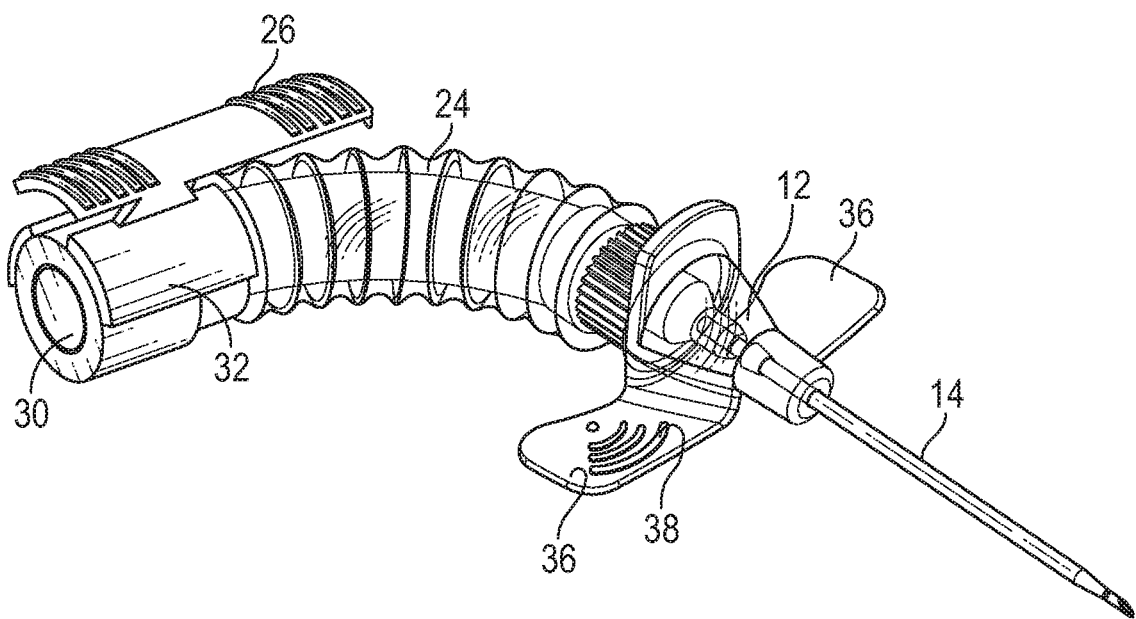
FIG. 3D is a perspective view of the catheter adapter of FIG. 3B with the extension tube extended and flexed.
Figure 3E:
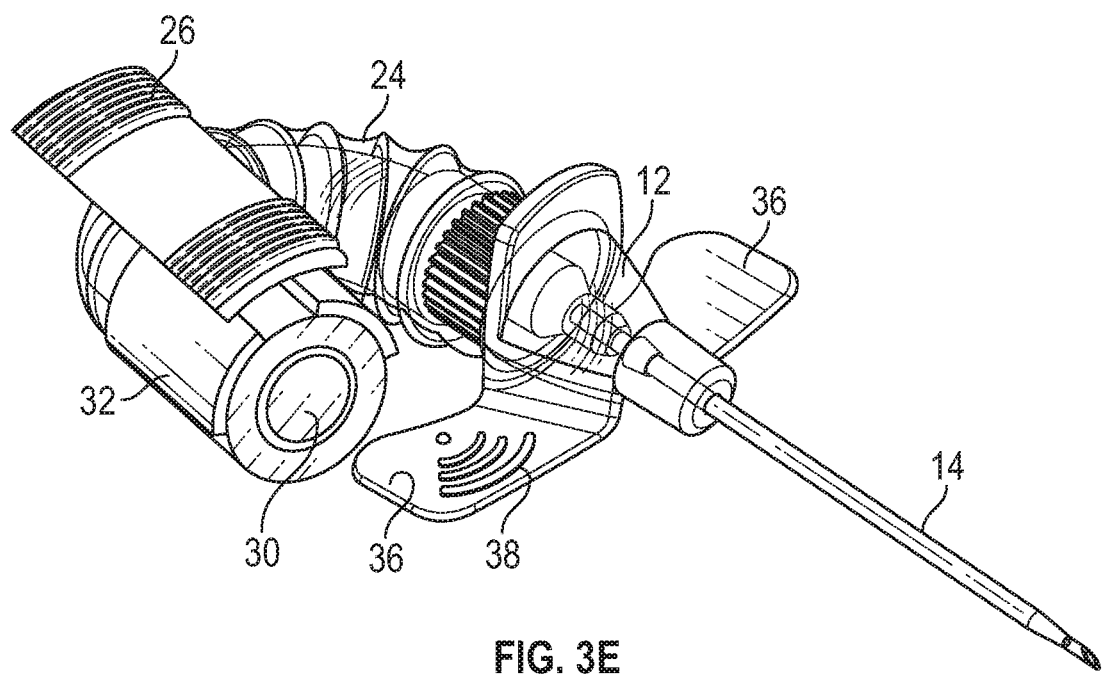
FIG. 3E is a perspective view of the catheter adapter of FIG. 3B with the extension tube extended and flexed.

Referring now to FIGS. 2D-2E, the catheter system 10 may include a septum 30. The septum 30 may be disposed within a proximal end of the extension tube 24. In some embodiments, the septum may be disposed within a septum holder 32 that is coupled to the extension tube 24. The locking mechanism 26 may couple to the septum holder 32 to secure the locking mechanism 26 to the extension tube. In some embodiments, the septum may be a 2-piece septum, 3-piece septum, or any suitable septum.

In some embodiments, the introducer needle 18 may pierce the septum 30 to extend through the catheter tube 14. Further, infusion devices may be coupled to the septum 30 to administer fluids to the patient. In some embodiments, a luer connector (not illustrated) may be coupled to the proximal end of the extension tube 24. The extension tube 24 may be coupled to the catheter adapter and/or the septum holder 32 or luer connector by laser welding. The extension tube 24 may be coupled to the catheter adapter 12 and or the septum holder 32 by an adhesive.

Referring now to FIGS. 3A-3E, the extension tube 24 may be corrugated. The corrugated extension tube may be extendable and/or compressible and the extension tube 24 may be flexible when extended. The flexible extension tube may improve patient comfort and require less securement for long indwell times. In some embodiments, the introducer needle is withdrawable through the extension tube when the extension tube is compressed, extended, or while the extension tube is being extended.

A patient may have low blood pressure making the withdrawal of blood more difficult because the blood may not flow into the catheter adapter 12 without assistance. The clinician may expand the extension tube 24 while withdrawing the introducer needle 18 to create a negative pressure within the catheter system 10 and/or the extension tube 24 such that a vacuum effect draws blood from the vein. An expansion of the extension tube 24 may not be necessary to draw out blood and the introducer needle 18 may be withdrawn without expanding the extension tube 24.

The introducer needle 18 may be withdrawn while the locking mechanism 26 is either engaged and/or disengaged. After the introducer needle 18 is withdrawn, the catheter adapter 12 and/or the extension tube 24 may be secured such that the distal end of the extension tube can be accessed for connecting other devices, sampling, and/or disinfecting the septum 30. The extension tube may be compressed and the locking mechanism 26 engaged prior to securing the catheter adapter 12 to the skin of the patient or prior to removing the catheter adapter.

The extension tube 24 may be resilient and retain shape when curved. As an example, the extension tube 24 may be extended and bent such that the extension tube is L-shaped, U-shaped, V-shaped, or otherwise redirected. The extension tube 24 may be configured to retain the bent shape. The bent shape may improve patient comfort as the catheter system 10 is secured for a period of indwell. In some applications, the extension tube 24 may be bent to provide a more secure and/or convenient coupling to fluid sources such as IV fluids and/or medical devices.

In some embodiments, the extension tube 24 may be repositioned from a previously different shape. The extension tube 24 may be compressed after being positioned in a bent configuration. In some embodiments, patency of the catheter tube 14 and/or the extension tube 24 may be evaluated by extending or compressing the extension tube. Expanding or compressing the extension tube causes fluid to flow into our out of the catheter tube. A clinician may use the force required to expand or contract the extension tube to determine the presence of an obstruction. In some embodiments, the extension tube may be configured to resist kinking. The corrugation of the extension tube 24 may be bendable without kinking, while still flexing to bent shapes and/or redirecting the extension tube. The locking mechanism 26 may be re-engaged after the extension tube 24 is compressed. In some embodiments, the compression of the extension tube 24 and/or the redirection of the extension tube may benefit the comfort of the patient by using less tape and/or securement material to secure the catheter adapter 12 or catheter system 10 for indwell.

Figure 4A:
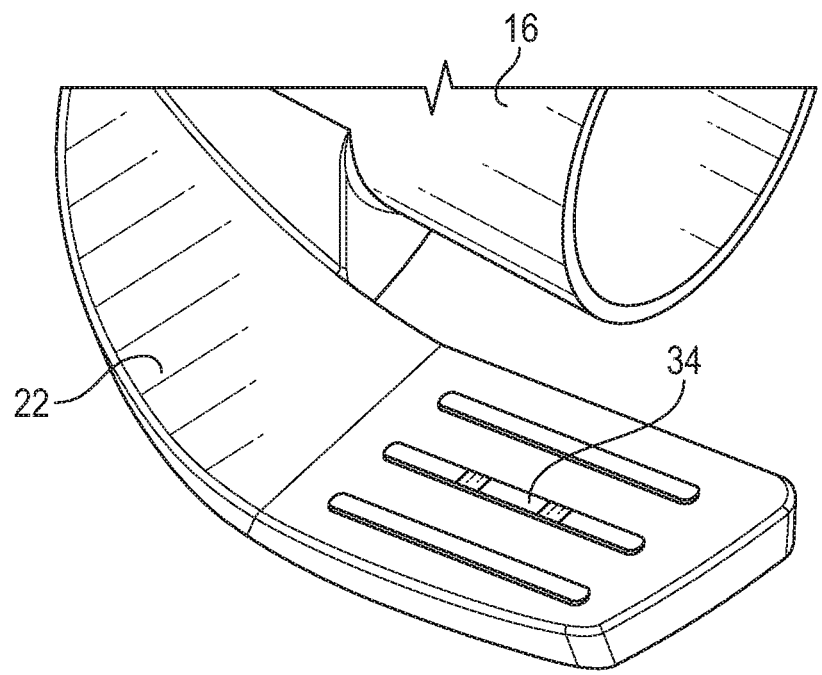
FIG. 4A is an upper perspective view of an example paddle grip, according to some embodiments.
Figure 4B:
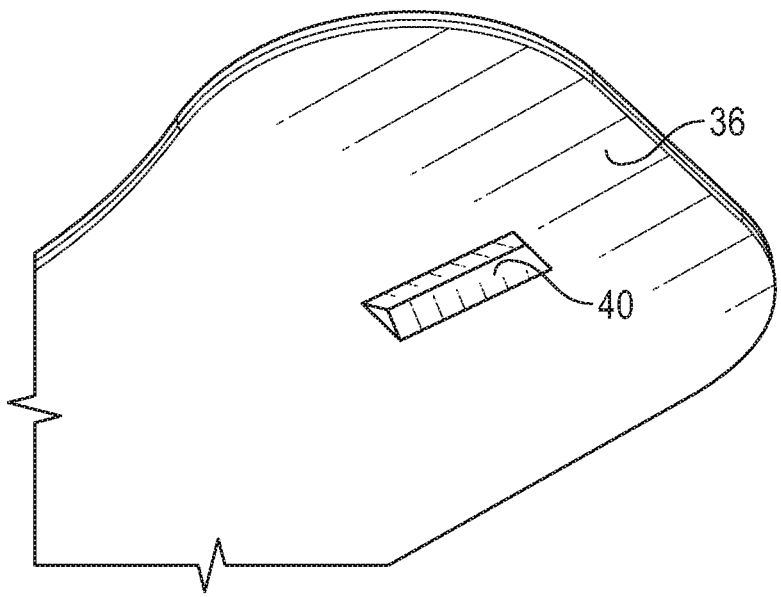
FIG. 4B is a lower perspective view of an example catheter wing extending from an example catheter adapter, according to some embodiments.
Figure 5A:
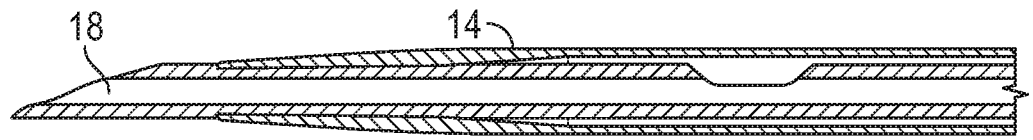
FIG. 5A is a cross-sectional view of an example needle in an insertion position within an example catheter tube, according to some embodiments.
Figure 5B:
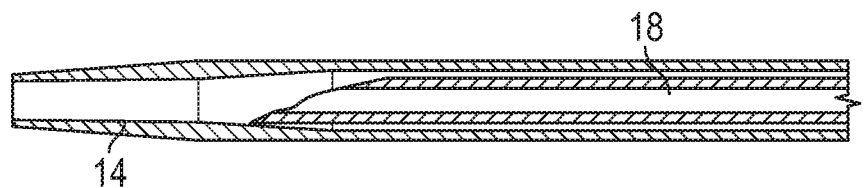
FIG. 5B is a cross-sectional view of an example needle in an intermediate position within an example catheter tube, according to some embodiments.

Referring now to FIGS. 4A-4B, the needle hub 16 may include a paddle grip 22 that may include a raised feature 34 on the upper surface of the paddle grip. The raised feature 34 may include a bump and/or a nub to enhance grip. The raised feature may include a ridge or ridges and/or other grip feature that assists the user with gripping the paddle grip 22. In some embodiments, the raised feature 34 may extend upward beyond the other grip feature of the paddle grip 22.

In some embodiments, the catheter adapter 12 includes at least one wing 36 that extends outwardly from the catheter adapter. The wings may stabilized the catheter adapter and simplify insertion of the catheter. In some embodiments, the catheter adapter 12 includes two wings extending from the catheter adapter. The wings may be constructed of flexible material. When the catheter adapter 12 is coupled to and/or nested within the needle hub 16, the at least one wing 36 of the catheter adapter may be situated on top of and/or contact the paddle grip 22. In some embodiments, the paddle grip 22 may extend distally beyond the wing 36 of the catheter adapter 12.

The wing 36 of the catheter adapter 12 may include and upper surface and a lower surface. The upper surface of the wing 36 may include a grip feature 38. In some embodiments, the grip feature 38 may enable the user to control the catheter adapter 12 as they administer the catheter system 10 to the patient. The grip feature 38 may include ridges and or nubs. In some embodiments, the lower surface of the wing 36 of the catheter adapter 12 may include a recess 40.

Referring now to FIGS. 4A 4B, the recess 40 may be configured to couple to the raised feature 34 on the paddle grip 22 when a tip of the introducer needle is withdrawn within the catheter tube. In some embodiments, the coupling of the raised feature 34 and the recess 40 provides a tactile indication to the user that the tip of the introducer needle 18 has been withdrawn into the catheter tube 14. The tactile indication may provide an indication to the user that the catheter tube 14 may be safely repositioned and/or further inserted into the vein of the patient without causing damage to the vein by the tip of the introducer needle 18. After the catheter tube 14 is placed in the desired indwell location, the raised feature 34 on the paddle grip 22 and the recess 40 may be decoupled and the introducer needle 18 may be completely withdrawn from the catheter adapter 12.

Figure 6:
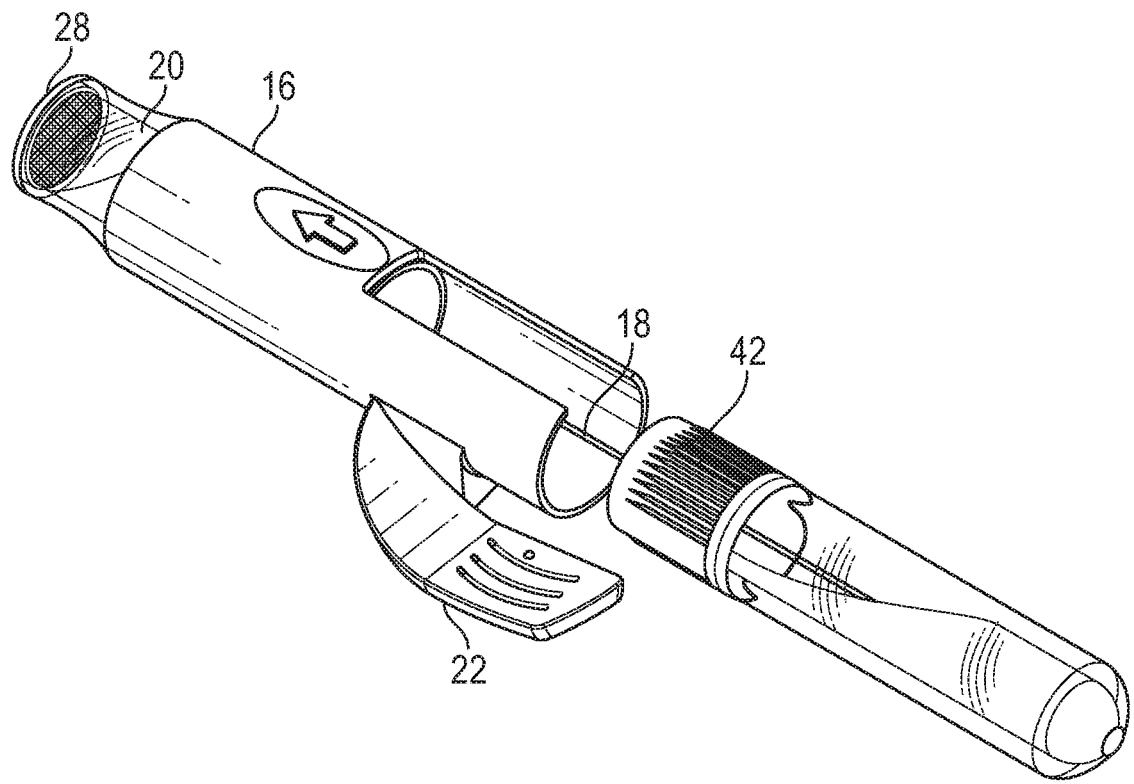
FIG. 6 is a perspective view of an example needle hub coupled to an example collection container, according to some embodiments.

Referring now to FIG. 6, the needle hub 16 may include the flash chamber 20 where, in response to the insertion of the catheter tube 14 into the vein of a patent, blood flows into the flash chamber 20. In some embodiments, the flash chamber 20 may be transparent to provide an indication to the user that the catheter tube 14 is positioned within the vein. The flash chamber 20 may confirm the proper placement of the catheter tube 14 within the vein. In some embodiments, the flash chamber may include an air vent 28 to remove air as it is displaced within the flash chamber 20 and/or catheter system 10 as blood flows into the catheter tube 14 and into the flash chamber 20. The air vent may include a membrane that filters air and may be impermeable to fluids.

The flash chamber may have a sufficient capacity to provide a blood sample. In some embodiments, the blood and/or fluid within the flash chamber 20 may be used as a sample. The flash chamber 20 may have a capacity between about 2 ml to about 3 ml. The blood within the flash chamber 20 may be sampled because the catheter system 10 has not been primed with priming fluid, which may diminish the sample. In using the blood within the flash chamber for a sample, a clinician would not need to stick the patient again after placing the catheter tube 14 within the vein. Further, the sample may be obtained without using other blood collection accessories. In some embodiments, the sample may be discharged through the introducer needle 18. For example, a sample tube 42 may be coupled to the flash chamber 20 to sample the blood and the introducer needle 18 may be placed into the sample tube 42 and a vacuum within the sample tube may draw the blood and/or fluid from the flash chamber into the sample tube. This method of sampling may be especially valuable for the care of pediatrics and/or neonates where placing a catheter and/or drawing blood may be more difficult.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment. It is to be understood that any of the embodiments of the present disclosure, or any portion(s) of any of the embodiments of the present disclosure, may be combined together in any number of different ways.

Similarly, it should be appreciated that in the above description of embodiments, various features are sometimes grouped together in a single embodiment, Figure, or description thereof for the purpose of streamlining the disclosure. This disclosure format, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Description Of Embodiments are hereby expressly incorporated into this Description Of Embodiments, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles set forth herein.

The phrases "connected to," "coupled to," "engaged with," and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

As defined herein, "substantially equal to" means "equal to," or within about a + or −10% relative variance from one another.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in the Figures, the Figures are not necessarily drawn to scale unless specifically indicated.

While specific embodiments and applications of the present disclosure have been illustrated and described, it is to be understood that the scope of the appended claims is not limited to the precise configuration and components disclosed herein. Various modifications, changes, and variations which will be apparent to those skilled in the art may be made in the arrangement, operation, and details of the apparatus and systems disclosed herein.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

The invention claimed is:

1. A catheter system, comprising:
a catheter adapter having a distal end, a proximal end, and a lumen extending therebetween, the catheter adapter further comprising a flange;
a catheter tube extending distally from the catheter adapter;
an extension tube, comprising a distal end and a proximal end, wherein the distal end of the extension tube is coupled to the proximal end of the catheter adapter, wherein the extension tube is extendable;
a septum holder coupled to the proximal end of the extension tube;
a septum disposed within the septum holder;
a lever extending from the septum holder, wherein a distal end of the lever comprises a lip configured to engage with the flange;
a needle hub removably coupled to the septum holder, wherein when the extension tube is in a compressed state, the extension tube is immediately surrounded by the needle hub and the lever; and
an introducer needle extending through the catheter tube, wherein a proximal end of the introducer needle is secured within the needle hub.

2. The catheter system of claim 1, wherein the extension tube is corrugated, such that the extension tube is flexible when extended.

3. The catheter system of claim 1, wherein the extension tube is resilient and retains shape when curved.

4. The catheter system of claim 1, in response to a depression of a proximal end of the lever, the lip is configured to disengaged from the flange of the catheter adapter.

5. The catheter system of claim 4, wherein the extension tube is compressed when the lip and the flange are engaged and is extendable when the lip and the flange are disengaged.

6. The catheter system of claim 1, wherein the introducer needle is withdrawable through the extension tube when the extension tube is compressed, extended, or while the extension tube is being extended.

7. The catheter system of claim 1, further comprising a luer connector coupled to the proximal end of the extension tube.

8. The catheter system of claim 1, wherein a flash chamber is disposed within the needle hub and extends in a proximal direction from a proximal end of the needle hub.

9. The catheter system of claim 1, wherein the needle hub further comprises a paddle grip.

10. The catheter system of claim 1, further comprising a flash chamber disposed within a proximal end of the needle hub and configured such that in response to insertion of the catheter tube into the vein of the patient, blood flows into the flash chamber.

11. The catheter system of claim 10, wherein the catheter adapter further comprises at least one wing that extends outwardly from the catheter adapter.

12. The catheter system of claim 11, wherein the needle hub further comprises a paddle grip, wherein the at least one wing comprises an upper surface and a lower surface, wherein the upper surface comprise a grip and the lower surface comprises a recess, wherein the recess couples with a grip on an upper surface of the paddle grip when a tip of the introducer needle is withdrawn within the catheter tube.

13. The catheter system of claim 10, wherein the flash chamber comprises an air vent.

14. The catheter system of claim 10, wherein the flash chamber has a capacity between about 2 ml to about 3 ml.

15. The catheter system of claim 10, wherein the flash chamber is transparent.

16. A catheter system, comprising:
a catheter adapter having a distal end, a proximal end, and a lumen extending therebetween, the catheter adapter further comprising a flange;
a catheter tube extending distally from the catheter adapter;
an extension tube, comprising a distal end and a proximal end, wherein the distal end of the extension tube is coupled to the proximal end of the catheter adapter, wherein the extension tube is extendable;
a septum holder coupled to the proximal end of the extension tube;
a septum disposed within the septum holder;
a lever extending from the septum holder, wherein a distal end of the lever comprises a lip configured to engage with the flange;
a needle hub removably coupled to the septum holder, wherein the needle hub comprises a cutout extending from a distal end of the needle hub, wherein the lever is disposed within the cutout, wherein when the extension tube is in a compressed state, the extension tube is immediately surrounded by the needle hub and the lever; and
an introducer needle extending through the catheter tube, wherein a proximal end of the introducer needle is secured within the needle hub.

\* \* \* \* \*